(12) United States Patent
Deguchi et al.

(10) Patent No.: US 7,070,988 B2
(45) Date of Patent: Jul. 4, 2006

(54) OLIGOSACCHARIDE SYNTHESIZER

(75) Inventors: Kisaburo Deguchi, Sapporo (JP);
Genzou Hirata, Hitachinaka (JP);
Masahito Ito, Hitachinaka (JP);
Hiroaki Nakagawa, Sapporo (JP);
Shinichiro Nishimura, Sapporo (JP)

(73) Assignee: Hitachi High Technologies Corporation, Tokyo (JP)

( * ) Notice: Subject to any disclaimer, the term of this patent is extended or adjusted under 35 U.S.C. 154(b) by 91 days.

(21) Appl. No.: 10/715,385

(22) Filed: Nov. 19, 2003

(65) Prior Publication Data

US 2004/0132176 A1 Jul. 8, 2004

(30) Foreign Application Priority Data

Nov. 20, 2002 (JP) .................................. 2002-335940
Oct. 29, 2003 (JP) .................................. 2003-368259

(51) Int. Cl.
*C12M 1/34* (2006.01)

(52) U.S. Cl. ................... 435/288.6; 435/289.1; 422/70; 422/82.05; 422/131; 422/212; 422/234

(58) Field of Classification Search ............... 422/70, 422/82.05, 131, 212, 234; 435/288.6, 289.1
See application file for complete search history.

(56) References Cited

U.S. PATENT DOCUMENTS 5,288,637 A   2/1994   Roth

FOREIGN PATENT DOCUMENTS

| JP | 60054398 | 3/1985 |
| JP | 5-500905 | 2/1993 |
| JP | 11-42096 | 2/1999 |
| WO | WO 03/004597 A1 | 1/2003 |

*Primary Examiner*—David Redding
(74) *Attorney, Agent, or Firm*—Dickstein Shapiro Morin & Oshinsky

(57) ABSTRACT

After various sugar nucleotide solutions and glycosyltransferases (or primers) have been mixed, they are introduced into a reaction tank (column) with primers (or glycosyltransferases) immobilized thereon. Then solutions coming out of the reaction tank are led to an ultrafiltration column. The oligosaccharide synthesizer according to the present invention is equipped with a flow path for ensuring that glycosyltransferases or primers separated by the ultrafiltration column are returned into a container for storing each solution in a sample injector.

7 Claims, 3 Drawing Sheets

OLIGOSACCHARIDE SYNTHESIZER

FIELD OF THE INVENTION

The present invention relates to a technique for oligosaccharide synthesis and separation processing, particularly to a oligosaccharide synthesizer for automating these types of processing.

Background of the Invention

A complex carbohydrate in a cell plays an important role in information transfer, identification among cells and recognition of a virus, cancer cell, blood type and others. Clarification of oligosaccharide functions is ranked as one of the major tasks that come after the study of genome. An oligonucleic acid and peptide synthesis method have been already established and automated. Oligosaccharide synthesis, however, has many problems yet to be solved.

In an effort to clarify the functions of oligosaccharide, establishment of oligosaccharide synthesis method and creation of an effective synthesizer have been long awaited. At present, the following three methods of oligosaccharide synthesis are practiced:

(1) Chemical synthesis
(2) Genetically recombinant cell or fermentation by microorganism
(3) Synthesis by glycosyltransferase The method (1) is characterized by complicated steps of synthesis, since sequential synthesis of target oligosaccharides is performed while protecting the OH group other than the OH group for chemical bondage. The method (2) is characterized in that, although a great numbers of target oligosaccharides can be obtained, subsequent steps of purification are complicated. The method (3) was developed to solve the problems encountered in the complicated steps in methods (1) and (2). It is disclosed in the Japanese Patent Laid-Open Publication No. 11-42096 (1999), for example. The method (3) is based on synthesis by selective glycosyltransferase, and does not require protection of the OH-group, as in method (1). Further, there is not much quantity of by-products, and purification process subsequent to synthesis is easy.

A oligosaccharide synthesizer is disclosed in the Japanese Patent Laid-Open No. 05-500905 (1993).

When an actual apparatus is used to carry out the synthesis of a oligosaccharide based on the aforementioned method (3) a batch system is used at present, wherein separation and purification of products are carried out for each step in the reaction of a plurality of sugars performed one after another. The next reaction is carried out after that. Manpower is essential to complete the entire processing, according to this method.

In the apparatus disclosed in the aforementioned Japanese Patent Laid-Open No. 05-500905, according to the order of sugars to be reacted, reaction columns and separation/purification means must be connected on a continuous basis.

To put it another way, even if the same sugars are reacted, the same number of reaction columns and separation/purification means as that of sugars are required. This requires a large-scale system of apparatuses.

Further, glycosyltransferase needed for reaction is generally very expensive. Any arrangement for permitting repeated use of glycosyltransferase is not taken into account.

SUMMARY OF THE INVENTION

The object of the present invention is to provide a oligosaccharide synthesizer that ensures effective synthesis of a plurality of sugars, and recovery and reuse of glycosyltransferase.

DESCRIPTION OF THE INVENTION

The present invention for achieving the aforementioned object is characterized in that, after various sugar nucleotide solutions and glycosyltransferases (or primers) have been mixed, they are introduced into a reaction tank where primers (or glycosyltransferases) are immobilized, whereby sugars are chemically bonded with primers one after another. After that, eluate is led into the ultrafiltration column from the reaction tank.

The present invention is also characterized by comprising a flow path for ensuring that the glycosyltransferase or primer separated by the ultrafiltration column is returned into a container for storing each solution in a sample injector.

This method permits effective synthesis of oligosaccharides. It also allows recovery of high-priced glycosyltransferase for reuse.

The present invention permits continuous and automatic synthesis of complicated oligosaccharides.

Further, it allows glycosyltransferases to be recovered for reuse.

DETAILED DESCRIPTION OF THE PREFERRED EMBODIMENTS

Embodiment 1

Figure 1:
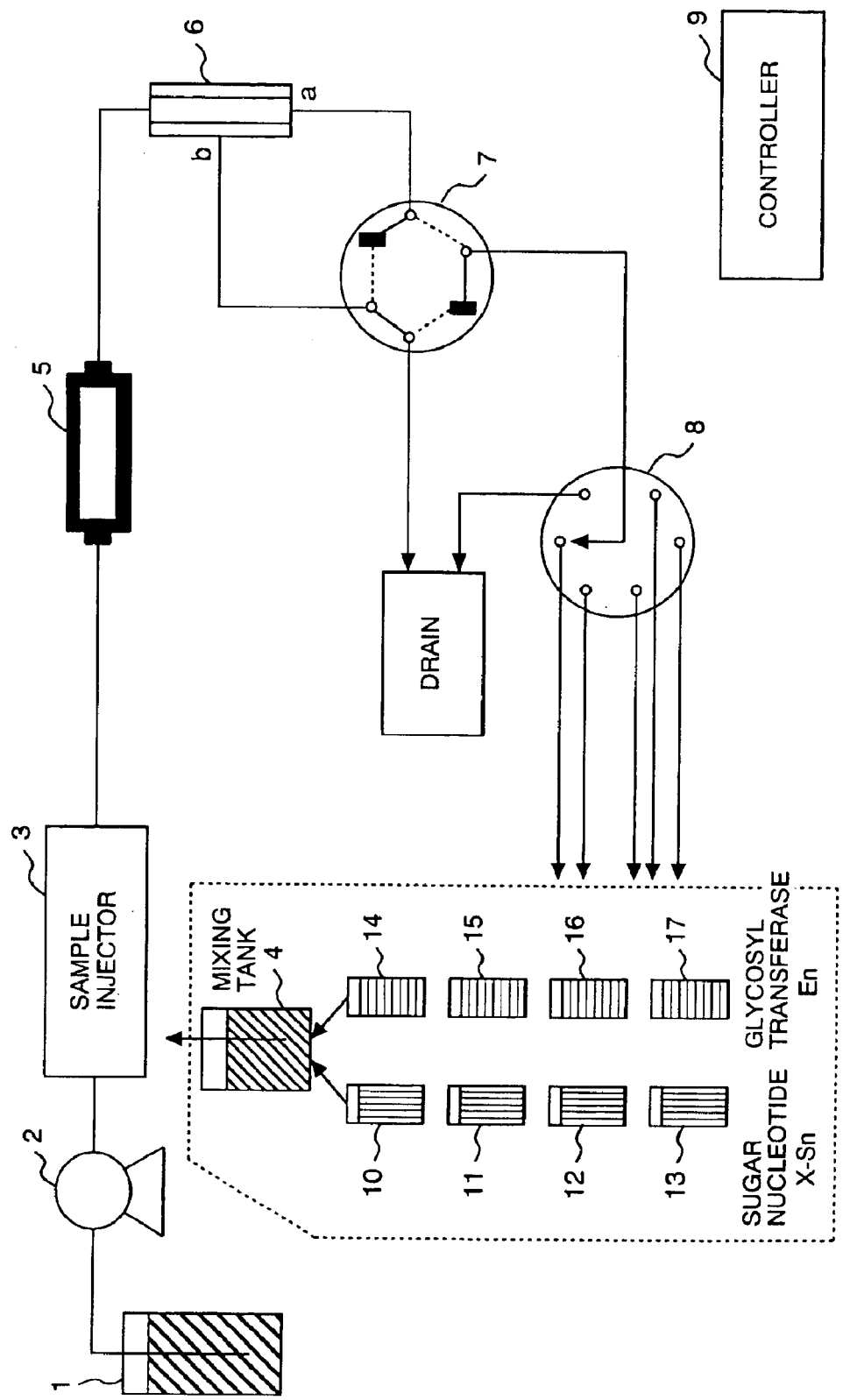
FIG. 1 is a system configuration diagram and flow diagram according to Embodiment 1.

FIG. 1 is a system configuration diagram according to Embodiment 1.

A oligosaccharide synthesizer comprises:

a buffer 1 best suited to reaction;

a pump 2 for feeding the buffer;

a mixing tank 4 for cooling and storing sugar nucleotides (X-Sn) 10 through 13 and glycosyltransferases (En) 14 through 17 and for mixing them after weighing;

a sample injector 3 for injecting the mixture into a flow path;

a reaction tank 5 for storing an immobilized primer (P);

an ultrafiltration column 6 for separating glycosyltransferase from unreacted sugar nucleotide (X-Sn) and nucleotide (X) as a product of reaction;

a six-way valve 7 for switching to determine whether the solution leaching out of the ultra-filtration column 6 should be discharged into the drain or an after-stage flow path switch valve 8;

a flow path switch valve 8 for leading the solution into the drain or each of the contains of glycosyltransferases (En) 14 through 17 of the sample injector 3; and a controller 9 for controlling these components.

The aforementioned ultrafiltration column 6 incorporates an ultra-filter and separates glycosyltransferase from unreacted sugar nucleotides (X-Sn) and nucleotides (X) as products of reaction, according to molecule size. Normally, the molecular weight of glycosyltransferase is of the order of tens of thousands, and those of the sugar nucleotides (X-Sn) and nucleotides (X) as products of reaction are of the order of several hundreds. This makes separation easy. The isolated glycosyltransferase is fed to the side "a" of the bottom of the ultrafiltration column 6, whereas the sugar nucleotides (X-Sn) and nucleotides (X) are fed to the side "b" on the lateral face of the ultrafiltration column 6.

Further, a black square in the six-way valve 7 indicates a sealed port. Accordingly, as shown in FIG. 1, when the portion indicated by the solid line forms a flow path, the solution running out of the side "a" of the ultrafiltration column 6 is stopped at the sealed position of the six-way valve 7.

In the present embodiment, the glycosyltransferase (En) refers to galactosyltransferase, N-acetyl glucosaminyltransferase, N-acetyl galactosaminyltransferase, fucosyltransferase, sialyltransferase, mannosyltransferase, etc.

Further, sugar nucleotide solution (X-Sn) refers to uridine-5'-diphosphogalactose, uridine-5'-diphospho-N-acetylglucosamine, uridine-5'-diphospho-N-acetylgalactosamine, guanosine-5'-diphosphofucose, guanosine-5'-diphosphomannose, cytidine-5'-monophospho-N-acetylneuraminic, etc.

Primer (P) denotes a water soluble polymer, and refers to a biopolymer such as protein, glycoprotein, glycopeptide, lipid, glycolipid, oligosaccharide and polysaccharide, as well as synthetic polymer such as polyacrylamide derivative described in the aforementioned Japanese Patent Laid-Open Publication No. 11-42096.

(Further, the primer having chemically bonded with sugar (Sn) hereinafter referred to as "primer (P-Sn)").

The primer (P) immobilized on a certain carrier of solid state is an immobilized primer (P). A thermostatic bath incorporating this immobilized primer (P) is a reaction tank 5. In the present embodiment, the primer (P) in the reaction tank 5 is bonded with sugar ($S_0$) in advance.

The following describes the operation of this apparatus with reference to FIG. 1:

Here primer P and sugars $S_1$, $S_2$ and $S_3$ are assumed to have been synthesized in the order of P-$S_1$-$S_2$-$S_3$. In practice, however, there is no restriction to the order of sugars $S_1$, $S_2$ and $S_3$.

The difference in the synthesis of sugars $S_1$, $S_2$ and $S_3$ is found in that they are assigned with the reaction temperature and reaction time best suited to each of them. Accordingly, when reaction is to be made in the order or P-$S_1$-$S_2$-$S_3$, the reaction temperature and reaction time in the reaction tank 5 are set in conformity to each sugar, and the following five steps are repeated three times in principle.

Further, when the optimum buffer is required in the synthesis of each, a plurality of buffers 1 are provided and a pump equipped with a low-pressure gradient function and capable of selecting a buffer is employed. This will easily meet the requirements.

Step 1:

Buffer 1 is fed by a pump 2 at a predetermined flow rate to wash the flow path. The six-way valve 7 and flow path switch valve 8 are set to the drain position to initialize the apparatus. In this case, the interior of the sample injector 3 is washed and the temperature of the reaction tank 5 is also set.

Step 2:

In the sample injector 3, a certain amount of sugar nucleotide (X-S1) 10 and its glycosyltransferase (E1) 14 are weighed and are mixed in the mixing tank 4. After that, the mixture is injected into the flow path.

Step 3:

The aforementioned mixture is introduced into the reaction tank 5 where primer (P) is immobilized, and is left to reaction at a certain temperature for a certain period of time. During reaction time, the flow rate of the pump 2 is constant or zero. When setting the flow rate of the pump, it is necessary to make sure that the sugar nucleotide (X-S1) 10 and its glycosyltransferase (E1) 14 do not flow out of the reaction tank 5 during the reaction time.

Step 4:

After expiration of reaction time, the solution coming out of the reaction tank 5 is led into the ultrafiltration column 6. It is fed for a certain time period, and is separated by an ultrafilter membrane. The solution coming out of the reaction tank 5 includes the glycosyltransferase (E1) 14, unreacted sugar nucleotide (X-S1) 10 and nucleotides (X) as products of reaction.

In this case, the six-way valve 7 functions as a flow path indicated by a solid line in FIG. 1. The filtered unreacted sugar nucleotide (X-S1) 10 and nucleotides (X) as products of reaction flow into the drain, and the glycosyltransferase (E1) 14 remains in the ultrafiltration column 6 since the flow path of the six-way valve 7 is sealed.

Step 5:

After separation, the six-way valve 7 is switched over to the flow path indicated by a dotted line in FIG. 1, and the glycosyltransferase (E1) 14 remaining in the ultrafiltration column 6 is fed to the side of the flow path switch valve 8. The flow path switch valve 8 is switched over to the flow path connected to a bottle for the glycosyltransferase (E1) 14. Then the glycosyltransferase (E1) 14 is captured and stored.

The aforementioned steps are repeated by replacing the sugar nucleotide (X-Sn) and glycosyltransferase (En), whereby the introduced sugars (Sn) are bonded to the primer (P) in the reaction tank 5 one after another, and a oligosaccharide is formed by synthesis.

To release the synthesized oligosaccharide from the solid state carrier upon termination of all reactions, an enzyme for this purpose is required. The enzyme for release is led from the sample injector 3, and is made to react in the reaction tank 5 for a certain time. After that, it is separated from the enzyme for release by the ultrafiltration column 6, and synthesized oligosaccharide ($S_0$-$S_1$-$S_2$-$S_3$) is captured on the drain side of the six-way valve 7.

The $S_0$ denotes the sugar first attached to the primer (P).

According to the present embodiment, efficient synthesis of a oligosaccharide can be carried out and the glycosyltransferases used for synthesis can be recovered for reuse.

Embodiment 2

Figure 2:
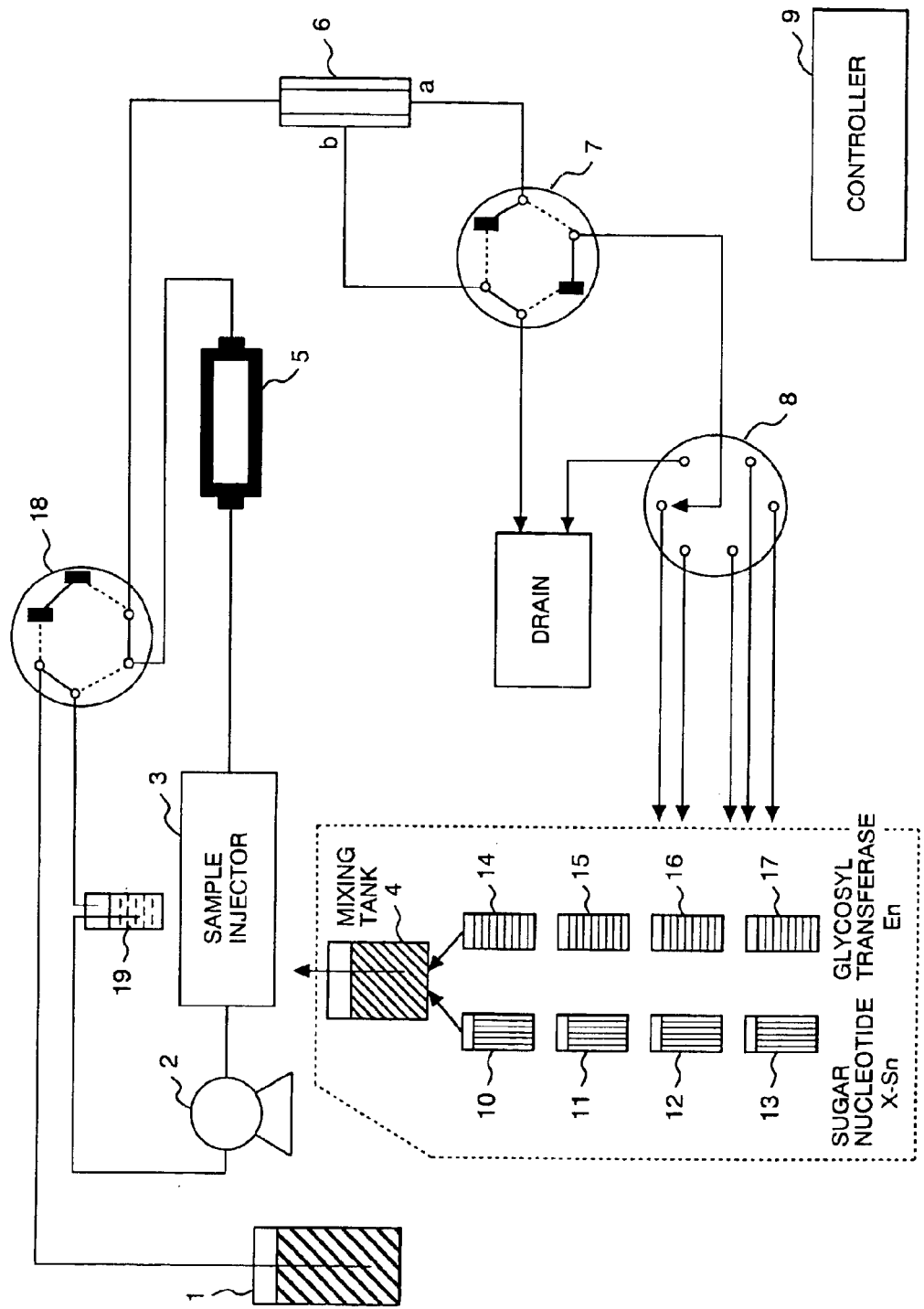
FIG. 2 is a system configuration diagram and flow diagram according to Embodiment 2.

FIG. 2 is a system configuration diagram of the Embodiment 2.

The oligosaccharide synthesizer contains:

a buffer 1 best suited to reaction;

a pump 2 for feeding the buffer;

a mixing tank 4 for cooling and storing sugar nucleotides (X-Sn) 10 through 13 and glycosyltransferases (En) 14 through 17 and for mixing them after weighing;

a sample injector 3 for injecting the mixture into a flow path;

a reaction tank 5 for storing an immobilized primer (P), a recycling six-way valve 18 for returning the solution coming out of the reaction tank 5, to the inlet of the pump 2;

a trap bottle 19 enclosed to once trap the solution coming out of the reaction tank 5, at the position just before the pump 2;

an ultrafiltration column 6 for separating glycosyltransferase from unreacted sugar nucleotide (X-Sn) and nucleotide (X) as a product of reaction;

a six-way valve 7 attached thereto;

a flow path switch valve 8 for recovering glycosyltransferase after ultrafiltration; and a controller 9 for controlling these components.

In the present embodiment, the primer (P) in the reaction tank 5 is bonded with the sugar ($S_0$) in advance. Further, a black square in the six-way valve 18 indicates a sealed port, as in the case of six-way valve 7.

The following describes the operation of this apparatus with reference to FIG. 2:

Here primer P and sugars $S_1$, $S_2$ and $S_3$ are assumed to be reacted in the order of $P-S_1-S_2-S_3$. In practice, however, there is no restriction to the order of sugars $S_1$, $S_2$ and $S_3$.

When synthesis is made in the order of $P-S_1-S_2-S_3$, the reaction temperature and reaction time in the reaction tank 5 are set in conformity to each sugar, and the following five steps are repeated three times in principle:

Step 1:

Buffer 1 is fed by a pump 2 at a predetermined flow rate to wash the flow path. The six-way valve 7 and flow path switch valve 8 are set to the drain position, and the recycling six-way valve 18 initializes the apparatus, using the flow path indicated by a solid line. In this case, the interior of the sample injector 3 is washed and the temperature of the reaction tank 5 is also set.

Step 2:

A certain amount of sugar nucleotide (X-S1) 10 and its glycosyltransferase are weighed and are mixed in the mixing tank 4. After that, the mixture is injected into the flow path by the sample injector 3.

Step 3:

The aforementioned mixture is introduced into the reaction tank 5 where primer (P) is immobilized, and is left to reaction at ascertain temperature for a certain period of time. During reaction time, the flow rate of the pump 2 is constant. The recycling six-way valve 18 is switched to form a flow path indicated by a dotted line.

Accordingly, the injected sugar nucleotide (X-S1) 10 and its glycosyltransferase (E1) 14 pass through the reaction tank 5 repeatedly during the reaction time.

Step 4:

After expiration of reaction time, the recycling six-way valve 18 is reset to the flow path indicated by a solid line. Then the solution coming out of the reaction tank 5 is led into the ultrafiltration column 6. It is fed for a certain time period, and is separated by an ultrafilter membrane. The solution coming out of the reaction tank 5 includes the glycosyltransferase (E1) 14, unreacted sugar nucleotide (X-S1) 10 and nucleotides (X) as products of reaction.

In this case, the six-way valve 7 functions as a flow path indicated by a solid line in FIG. 1. The filtered unreacted sugar nucleotide (X-S1) 10 and nucleotides (X) as products of reaction flow into the drain, and the glycosyltransferase (E1) 14 remains in the ultrafiltration column 6 since the flow path of the six-way valve 7 is sealed.

Step 5:

After separation, the six-way valve 7 is switched over to the flow path indicated by a dotted line in FIG. 2, and the glycosyltransferase (E1) remaining in the ultrafiltration column 6 is fed to the side of the flow path switch valve 8. The flow path switch valve 8 is switched over to the flow path connected to a bottle for the glycosyltransferase (E1) 14. Then the glycosyltransferase (E1) 14 is captured and stored.

The synthesized oligosaccharide ($P-S_1-S_2-S_3$) is separated from the solid state carrier upon termination of all reactions, and is captured in the same manner as in Embodiment 1.

The major difference from the Embodiment 1 is found in the Step 3. In the present embodiment, the injected sugar nucleotide and glycosyltransferase are fed into the reaction tank 5 repeatedly at a certain flow rate, whereby permitting effective agitation and promoting reactions. Further, what should be taken care of in the aforementioned Embodiment 1, i.e. the relationship between reaction time and flow rate, need not be taken in account, with the result that easy operation is ensured.

Embodiment 3

Figure 3:
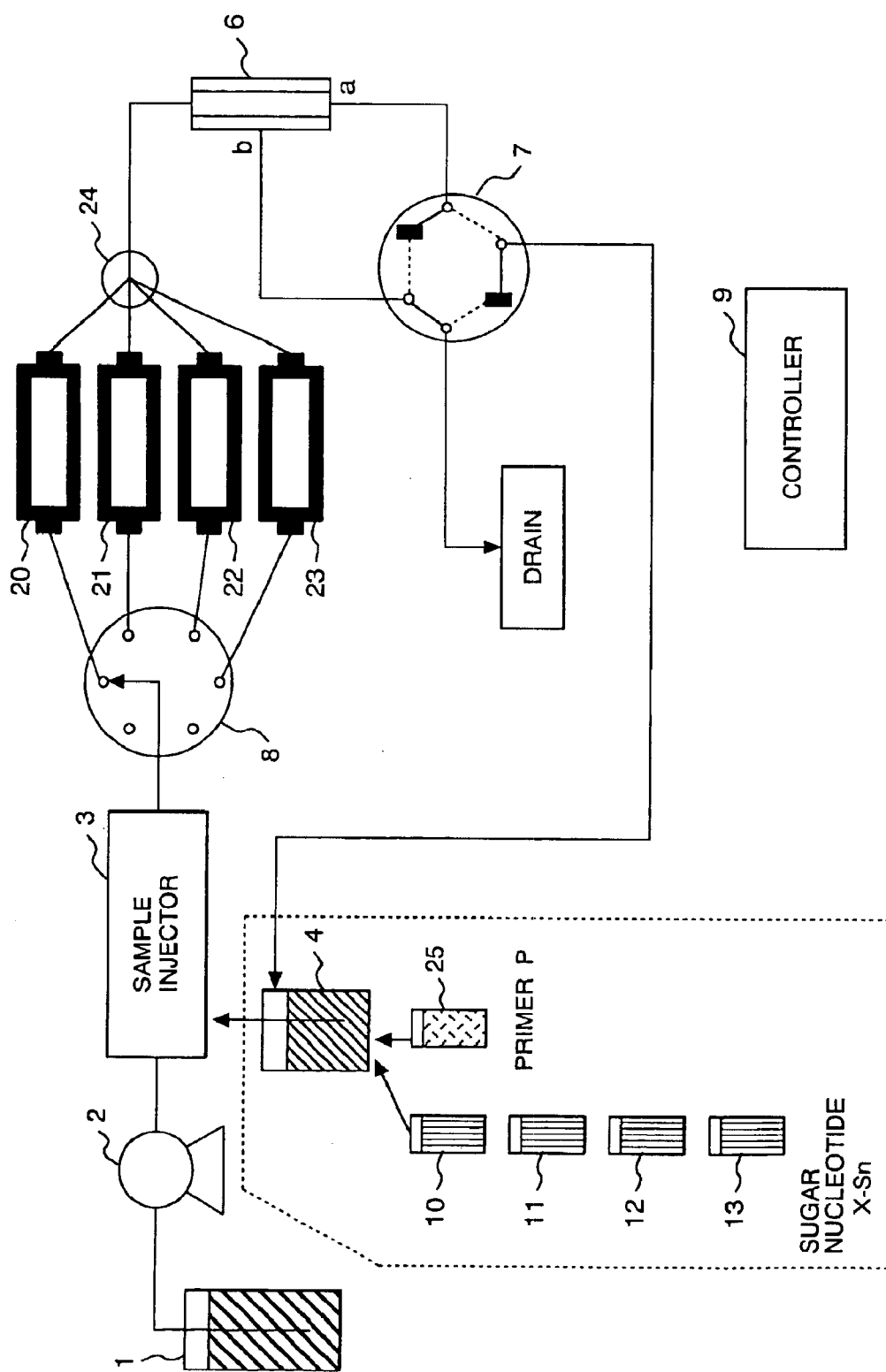
FIG. 3 is a system configuration diagram and flow diagram according to Embodiment 3.

FIG. 3 is a system configuration diagram representing the present embodiment.

The oligosaccharide synthesizer comprises:

a buffer 1 best suited to reaction;

a pump 2 for feeding the buffer;

a mixing tank 4 for cooling and storing sugar nucleotides (X-Sn) 10 through 13 and for mixing them with the primer (P) 25 bonded with sugar ($S_0$) in advance after weighing;

a sample injector 3 for injecting the mixture into a flow path;

reaction columns 20 through 23 having a temperature regulating function for immobilizing glycosyltransferases;

a flow path switch valve 8 for selecting a flow path leading to the reaction column;

a manifold 24;

an ultrafiltration column 6 for separating primer (P) and primer (P-Sn) from unreacted sugar nucleotide (X-Sn) and nucleotide (X) as a product of reaction;

a six-way valve 7 attached thereto; and a controller 9 for controlling these components.

In the present embodiment as well, the primer (P) 25 in the reaction tank 5 is bonded with the sugar ($S_0$) in advance.

The difference from the Embodiments 1 and 2 is that primer (P) is immobilized to the reaction tank 5 in Embodiments 1 and 2, whereas glycosyltransferases are immobilized in the present embodiment. Further, glycosyltransferases are recovered in Embodiments 1 and 2, while primer (P) is recovered in the present embodiment. It should be noted that several types of glycosyltransferases are used in conformity to the type of the sugar to be synthesized. This requires use of a plurality of reaction columns where glycosyltransferases are immobilized.

In the present embodiment, the aforementioned ultrafiltration column 6 separates the primer (P) from unreacted sugar nucleotide (X-Sn) and nucleotide (X) as a product of reaction according to molecular size by an ultrafilter membrane. The separated primer (P) and primer (P-Sn) are fed to the side "a" of the ultrafiltration column 6, and the sugar nucleotide (X-Sn) and nucleotide (X) are fed to the side "b" of the ultrafiltration column 6.

The following describes the operation of this apparatus with reference to FIG. 3:

Here primer P and sugars $S_1$, $S_2$ and $S_3$ are assumed to be synthesized in the order of $P-S_1-S_2-S_3$. Further, the glycosyltransferases for catalyzing the transfer reaction of sugars $S_1$, $S_2$ and $S_3$ are assumed to be immobilized in the reaction columns 20 through 23. In practice, however, there is no restriction to the order of sugars $S_1$, $S_2$ and $S_3$.

When synthesis is made in the order of $P-S_1-S_2-S_3$, the reaction temperature and reaction time in the reaction columns 20 through 23 are set in conformity to each sugar, and the following five steps are repeated three times in principle:

Step 1:

Buffer 1 is fed by a pump 2 at a predetermined flow rate to wash the flow path. The six-way valve 7 initializes the apparatus, using the flow path indicated by a solid line. In this case, the interior of the sample injector 3 is washed. Further, the flow paths leading to the reaction columns 20 through 23 to be used are selected by the flow path switch valve 8, and the temperature of the reaction columns is set.

Step 2:

A certain amount of sugar nucleotide (X-S1) 10 and primer (P) 25 are weighed and are mixed in the mixing tank 4. After that, the mixture is injected into the flow path by the sample injector 3.

Step 3:

The aforementioned mixture is introduced into a reaction column where glycosyltransferase is immobilized, for example, reaction column 20, and is left to reaction at a certain temperature for a certain period of time.

Step 4:

After expiration of reaction time, the solution coming out of the reaction column 20 is led into the ultrafiltration column 6. It is fed for a certain time period, and is separated by an ultrafilter membrane. The solution coming out of the reaction column 20 includes the primer (P-S1) formed by the primer (P) bonded with sugar ($S_1$), and unreacted sugar nucleotide (X-S1) 10 and nucleotides (X) as products of reaction.

In this case, the six-way valve 7 functions as a flow path indicated by a solid line in FIG. 3. The filtered unreacted sugar nucleotide (X-S1) 10 and nucleotides (X) as products of reaction flow into the drain, and the primer (P-S1) remains in the ultrafiltration column 6 since the flow path of the six-way valve 7 is sealed. The molecular weight of primer (P) is of the order of tens of thousands or hundreds of thousands, while those of the sugar nucleotides (X-S1) and nucleotides (X) are of the order of several hundreds. This makes separation easy.

Step 5:

After separation, the six-way valve 7 is switched over to the flow path indicated by a dotted line in FIG. 3, and the primer (P-S1) remaining in the ultrafiltration column 6 is recovered into the mixing tank 4.

When the primer (P-S1) has been recovered, it goes back to step 1, and the primer (P-S1) is mixed with the sugar nucleotide (X-S2) 11 and is fed to the reaction column. This processing is repeated until the termination of the planned sugar synthesis.

To release the synthesized oligosaccharide from the primer (P) upon termination of all reactions, an enzyme for this purpose is required. The flow path switch valve 8 is used to switch the flow path over to the reaction column (e.g. reaction column 23) where an enzyme for oligosaccharide release is immobilized. The primer ($P-S_1-S_2-S_3$) as a final product led from the sample injector 3 is made to react for a certain time in the reaction column 23 and the oligosaccharide is released from the primer. After that, it is separated from the primer by the ultrafiltration column 6 and the synthesized oligosaccharide ($S_0-S_1-S_2-S_3$) is captured on the drain side of the six-way valve 7. The molecular weight of oligosaccharide ($S_0-S_1-S_2-S_3$) is of the order of thousands, while that of the primer is of the order of tens of thousands or hundreds of thousands. This makes separation easy.

Here $S_0$ denotes the sugar first attached to the primer (P).

According to the present embodiment, oligosaccharide synthesis reaction can be repeated while recovering the primer into the mixing tank 4, thereby ensuring efficient synthesis of oligosaccharides.

What is claimed is:

1. A oligosaccharide synthesizer comprising:
   a container for storing buffer solution;
   a pump for feeding buffer solution;
   a sample injector comprising a container for storing a sugar nucleotide solution and a container for storing glycosyltransferase, said injector for mixing said sugar nucleotide solution and said glycosyltransferases and for injecting the mixture into a flow path for feeding said buffer solution;
   a reaction tank where a primer is immobilized, said tank used for reaction between solution injected out of said sample injector and said primer;
   an ultrafiltration column for separating said glycosyltransferase from sugar nucleotide and nucleotide; and
   a collection flow path for feeding said glycosyltransferase flowing out of said ultrafiltration column, into the container for storing glycosyltransferase of said sample injector.

2. The oligosaccharide synthesizer according to claim 1 further comprising:
   a plurality of said containers for storing the buffer solution;
   a plurality of said collection flow paths provided in accordance with the number of said containers for storing the buffer solution; and
   a collection flow path switch valve for feeding the solution coming out of said ultrafiltration column into one of said collection flow paths.

3. The oligosaccharide synthesizer according to claim 1 comprising:
   a circulating flow path switch valve arranged between said ultrafiltration columns in order to switch between the flow paths of various sections;
   said circulating flow path switch valve characterized by switching between a first flow path for circulation through the reaction tank, circulating flow path switch valve, pulp, sample injector and reaction tank; and a second flow path for circulation through the buffer solution container, circulating flow path switch valve, pump, sample injector, reaction tank and ultrafiltration column.

4. A oligosaccharide synthesizer comprising:
   a container for storing buffer solution;
   a pump for feeding buffer solution;
   a sample injector further comprising:
   a container for storing a sugar nucleotide solution,
   a container for storing a primer, and
   a mixing tank for mixing the sugar nucleotide solution with said primer;
   wherein the solution mixed by said mixing tank being injected into the flow path for feeding said buffer solution by said sample injector;

a reaction tank where said primer is immobilized, said tank being used for reaction between solution injected out of said sample injector and said primer;

an ultrafiltration column for separating said primer from sugar nucleotide and nucleotide or oligosaccharide;

a first flow path for feeding the primer coming out of the ultrafiltration column, into the primer container of said sample injector; and a second flow path for feeding the sugar nucleotide and nucleotide or oligosaccharide coming out of the ultrafiltration column, into a drain.

5. The oligosaccharide synthesizer according to claim 4 comprising:

a plurality of said reaction tanks, a switch valve arranged between a plurality the said reaction tanks in order to feed the solution injected out of said sample injector, into any one of the reaction tanks.

6. The oligosaccharide synthesizer according to claim 5 characterized in that an enzyme for releasing oligosaccharide from said primer is immobilized on one of said reaction columns.

7. The oligosaccharide synthesizer according to claim 6 characterized in that, after solution has passed through the reaction tanks where said enzyme is immobilized, oligosaccharide is collected from said drain.

* * * * *